(12) United States Patent
Sakai et al.

(10) Patent No.: US 9,103,841 B2
(45) Date of Patent: Aug. 11, 2015

(54) METHOD FOR DETERMINING GLUCAGON-LIKE PEPTIDE-1, AND KIT FOR USE IN SAID METHOD

(75) Inventors: China Sakai, Minato-ku (JP); Shigeru Tashiro, Minato-ku (JP)

(73) Assignee: LSI MEDIENCE CORPORATION, Tokyo (JP)

( * ) Notice: Subject to any disclaimer, the term of this patent is extended or adjusted under 35 U.S.C. 154(b) by 0 days.

(21) Appl. No.: 14/238,555

(22) PCT Filed: Aug. 24, 2012

(86) PCT No.: PCT/JP2012/071432
§ 371 (c)(1),
(2), (4) Date: Feb. 12, 2014

(87) PCT Pub. No.: WO2013/027823
PCT Pub. Date: Feb. 28, 2013

(65) Prior Publication Data
US 2014/0199711 A1    Jul. 17, 2014

(30) Foreign Application Priority Data
Aug. 25, 2011  (JP) ................................ 2011-183791

(51) Int. Cl.
G01N 33/53    (2006.01)
G01N 33/74    (2006.01)

(52) U.S. Cl.
CPC .......... *G01N 33/74* (2013.01); *G01N 2333/605* (2013.01)

(58) Field of Classification Search
None
See application file for complete search history.

(56) References Cited

U.S. PATENT DOCUMENTS

| | | | | |
|---|---|---|---|---|
| 4,444,879 A | * | 4/1984 | Foster et al. | 435/7.95 |
| 4,703,001 A | * | 10/1987 | Vodian et al. | 435/5 |
| 2008/0193997 A1 | * | 8/2008 | Matsumoto et al. | 435/186 |

FOREIGN PATENT DOCUMENTS

| | | |
|---|---|---|
| EP | 0713096 | 5/1996 |
| JP | 2008-104870 | 5/2008 |

OTHER PUBLICATIONS

Orback, (ELISA analysis of peptides and proteins in stabilized plasma, Molecular Biotechnology Programme, Uppsala University School of Engineering, May 2011, pp. 7-39).*
International Search Report issued Sep. 25, 2012 in International (PCT) Application No. PCT/JP2012/071432, Sep. 25, 2012.
Pridal et al., "Comparison of sandwich enzyme-linked immunoadsorbent assay and radioimmunoassay for determination of exogenous glucagon-like peptide-1(7-36)amide in plasma", Journal of Pharmaceutical and Biomedical Analysis, vol. 13, 1995, pp. 841-850.
Heijboer et al., "Analysis of glucagon-like peptide 1; what to measure?", Clinica Chimica Acta, vol. 412, 2011, pp. 1191-1194.
Deacon et al., "Immunoassays for the incretin hormones GIP and GLP-1", Best Practice & Research Clinical Endocrinology & Metabolism, vol. 23, 2009, pp. 425-432.
International Preliminary Report on Patentability issued Feb. 25, 2014 and Written Opinion of the International Searching Authority issued Sep. 25, 2012 in International (PCT) Application No. PCT/JP2012/071432, Sep. 25, 2012.
Chandarana et al., "Subject Standardization, Acclimatization, and Sample Processing Affect Gut Hormone Levels and Appetite in Humans", Gastroenterology, vol. 136, No. 7, pp. 2115-2126, (2009).
Stengel et al., "The RAPID Method for Blood Processing Yields New Insight in Plasma Concentrations and Molecular Forms of Circulating Gut Peptides", Endocrinology, vol. 150, No. 11, pp. 5113-5118, (2009).
Extended European Search Report issued Apr. 28, 2015 in corresponding European Patent Application No. 12826318.3.

* cited by examiner

*Primary Examiner* — Gary W Counts
(74) *Attorney, Agent, or Firm* — Wenderoth, Lind & Ponack, L.L.P.

(57) ABSTRACT

Provided is a method of measuring the presence and/or the amount of glucagon-like peptide-1 (GLP-1) in a sample, which method is characterized by comprising the step of treating the sample in advance with an acidic solution, and a kit of measuring the presence and/or an amount of GLP-1 in a sample, the kit containing (a) the acidic solution, (b) an antibody specific to GLP-1, and (c) an instruction manual.

9 Claims, 4 Drawing Sheets

SEQUENCE LISTING

```
<160> NUMBER OF SEQ ID NOS: 6

<210> SEQ ID NO 1
<211> LENGTH: 30
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 31
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 28
<212> TYPE: PRT
<213> ORGANISM: Homo sapiens

<400> SEQUENCE: 3

Glu Gly Thr Phe Thr Ser Asp Val Ser Ser Tyr Leu Glu Gly Gln Ala
1               5                   10                  15
```

```
Ala Lys Glu Phe Ile Ala Trp Leu Val Lys Gly Arg
            20                  25

<210> SEQ ID NO 4
<211> LENGTH: 29
<212> TYPE: PRT
<213> ORGANISM: Homo sapiens

<400> SEQUENCE: 4

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly Arg Gly
            20                  25

<210> SEQ ID NO 5
<211> LENGTH: 37
<212> TYPE: PRT
<213> ORGANISM: Homo sapiens

<400> SEQUENCE: 5

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 6
<211> LENGTH: 36
<212> TYPE: PRT
<213> ORGANISM: Homo sapiens

<400> SEQUENCE: 6

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg
        35
```

METHOD FOR DETERMINING GLUCAGON-LIKE PEPTIDE-1, AND KIT FOR USE IN SAID METHOD

TECHNICAL FIELD

The present invention relates to a method of readily and accurately measuring glucagon-like peptide-1 (GLP-1) and a kit used therein.

BACKGROUND ART

In development of pharmacological agents aiming at inhibiting the activity of dipeptidyl peptidase IV (hereinafter, may be referred to as "DPP-IV") or pharmaceutical products (mainly drugs for diabetes) with glucagon-like peptide-1 (GLP-1) as a pharmacological agent, the measurement of the concentration of GLP-1 that is active in the blood (GLP-1 (active)) or the concentration of total GLP-1 (GLP-1 (total)) is often carried out for the purpose of measuring parameters for drug efficacy evaluation and the concentration of drugs.

Mechanisms of action of DPP-IV inhibitors involve increasing the concentration active form GLP-1, which has a property of being decomposed by DPP-IV, by inhibiting the activity of DPP-IV and promoting insulin secretion by GLP-1 to promote utilization of sugars. Thus, by measuring the concentration of GLP-1, effects of the action of the DPP-IV inhibitor can be evaluated.

As the active form GLP-1, there are known to be GLP-1 (7-36 Amide) and GLP-1 (7-37). Measurement of these is widely carried out by an immunoassay method using a specific antibody (ELISA method: a kit manufactured by Merck Millipore or the like). However, non-specific reactions often take place and it has thus been known that, in order to measure an accurate concentration in the blood plasma, a certain pretreatment is required to be carried out to get rid of the non-specific reaction (Non-patent Document 1). In general, what is considered as the non-specific reaction in the ELISA method is one ascribed to a sample such as the blood, one ascribed to an antibody and/or reagent, one ascribed to a microtiter plate, or the like. In conventional methods, the non-specific reactions are considered to be ascribed to the sample. These are removed from the sample by a pretreatment method using a column and then the ELISA method is carried out. This pretreatment method separates substances causing the non-specific reaction from GLP-1 by a solid phase column or ethanol extraction operation. Yet, an amount of blood plasma necessary for one examination is as high as 300 μL; and the method requires complicated operations and time, which operations include reagent preparation, separation operation, drying to solidify using a nitrogen gas, and re-dissolution; and also requires the skill of those who are involved in the operations. From the above, it cannot be said that the conventional method is a simple and low-cost measurement method. Further, because a loss of 20 to 30% of GLP-1 in a sample is unavoidable by this pretreatment operation, the measurement value of GLP-1 is considered to be about 70 to 80% based on a true value, which has been problematic in terms of accuracy as well.

PRIOR ART REFERENCES

Non-Patent Documents

Non-patent Document 1: CF. Deacon, J J. Holst/Best Practice & Research Clinical Endocrinology & Metabolism 23 (2009) 425-432

SUMMARY OF THE INVENTION

An object of the present invention is to provide a method and kit that are able to solve the above problems and whereby the measurement of GLP-1 in a sample can be simply and accurately carried out in a situation suitable for practical use in a clinical study.

The present inventors intensively studied to allow for the measurement that clears up the loss due to the recovery operation by subjecting a sample to an acid treatment without using a solid phase column, that provides accurate measurement values with the influence of non-specific reactive substances being eliminated, as well as that is low in cost and simple. To be specific, no use of the solid phase column made it unnecessary to carry out complicated operations including washing, elution, drying to solidify using a nitrogen gas, and re-dissolution. A period of time required for the pretreatment of the sample was shortened by about 4.5 hours; and the amount of required blood plasma was able to be cut in half. In particular, because a examination facility is required to process a number of samples, the present invention is able to dramatically improve the processing capacity. Further, because the method is simple and convenient and does not require a specialized technique at the time of operation, no matter who carries out the method, a stable measurement can be carried out. On the basis of these findings, the present invention was completed.

Further, an acid treatment is known to have an effect such as rendering inactive depending on an amino acid sequence; and in general the treatment is used in a limited way, as exemplified by the use thereof in purification of a highly active (or stable) antibody or the like. It was an unexpected effect that GLP-1 was stable whereas the non-specific reactive substances were denatured or the like in the acid treatment of the present invention, thereby inhibiting non-specific reactions in the method of measuring the concentration of GLP-1 and enabling an accurate measurement of the concentration of GLP-1.

Accordingly, the present invention is as follows:

(1) A method of measuring the presence and/or an amount of glucagon-like peptide-1 (GLP-1) in a sample, comprising the step of treating the sample in advance with an acidic solution.

(2) The method according to (1), wherein the acidic solution comprises at least one of glycine, hydrochloric acid, acetic acid, guanidine hydrochloride, sulfuric acid, and phosphoric acid.

(3) The method according to (1) or (2), wherein the sample is blood.

(4) The method according to any of (1) to (3), wherein the method of measuring GLP-1 is an enzyme immunoassay or a competitive radioimmunoassay.

(5) A kit of measuring the presence and/or an amount of GLP-1 in a sample, comprising: (a) an acidic solution, (b) an antibody specific to GLP-1, and (c) an instruction manual.

The "GLP-1" includes ones generated from full length GLP-1 such as active form GLP-1, inactive form GLP-1, or full length GLP-1

The amino acid sequence of each of "GLP-1" is shown below.

```
Active form GLP-1
GLP-1(7-36) Amide:
                                           (SEQ ID NO: 1)
HAEGTFTSDVSSYLEGQAAKEFIAWLVKGR-CONH2
```

```
-continued
GLP-1(7-37):
                                         (SEQ ID NO: 2)
HAEGTFTSDVSSYLEGQAAKEFIAWLVKGRG Inactive form GLP-1
GLP-1(9-36) Amide:
                                         (SEQ ID NO: 3)
EGTFTSDVSSYLEGQAAKEFIAWLVKGR-CONH2

GLP-1(9-37):
                                         (SEQ ID NO: 4)
EGTFTSDVSSYLEGQAAKEFIAWLVKGRG

Full length GLP-1
GLP-1(1-37):
                                         (SEQ ID NO: 5)
HDEFERHAEGTFTSDVSSYLEGQAAKEFIAWLVKGRG GLP-1(1-36) Amide:
                                         (SEQ ID NO: 6)
HDEFERHAEGTFTSDVSSYLEGQAAKEFIAWLVKGR-CONH2
```

Of the above "GLP-1", active form GLP-1 has an incretine action. The present invention is preferably used for active form GLP-1.

Effect of the Invention

According to the present invention, non-specific reactions in a sample at the time of GLP-1 measurement can be inhibited with high efficiency and such a GLP-1 can be simply and accurately measured. By employing the present invention, the amount of sample subjected to the measurement can be reduced to about half, as compared with the amount that is conventionally used; and regardless of the level of skills of those who carry out measurement, the measurement of GLP-1 becomes possible to be carried out accurately and at low cost. It is also of great use in clinical practice that no cumbersome operations are required and a uniformed measurement can be simply and conveniently carried out.

EMBODIMENTS FOR CARRYING OUT THE INVENTION

Figure 1:
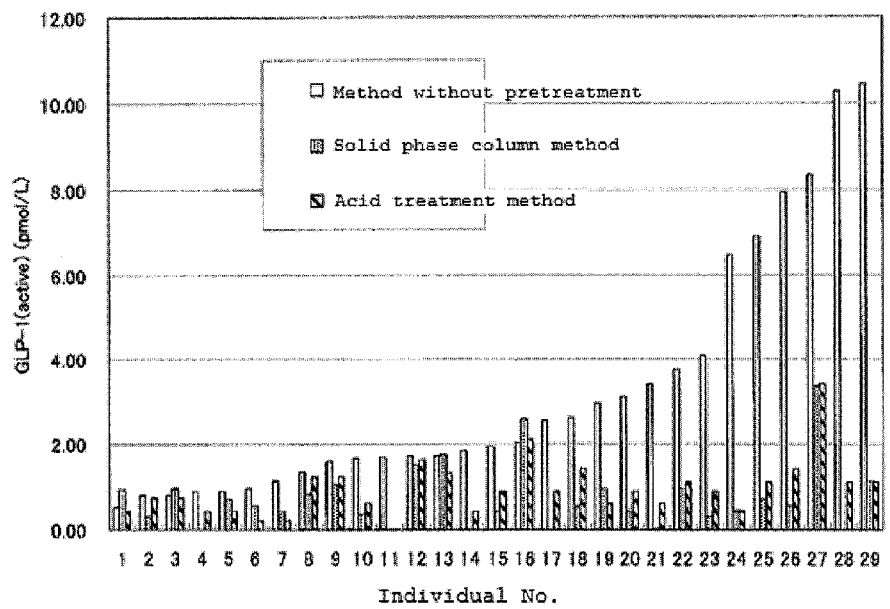
FIG. 1 shows the result obtained by treating the fasting blood plasma by a method without pretreatment, a solid phase column method, or an acid treatment method for 29 cases of healthy subjects and by subsequently measuring the concentration of active form GLP-1.

The present invention is characterized by, in measurement of GLP-1 in a sample, subjecting the sample in advance to an acid treatment and then subjecting the resultant the above-mentioned measurement.

The present invention can be used in a known method of measuring the presence and/or amount (concentration) of GLP-1 in a sample. That is, the measurement method of the present invention may be the same as common methods of measuring GLP-1 except that the sample of the present invention is subjected in advance to an acid treatment and subjected the resultant to the above-mentioned measurement. Examples of the measurement method include an immunological method and an instrumental analysis method, among them preferred is an immunological method.

What is carried out as the measurement of the amount of GLP-1 is measurement intended only for active form GLP-1 that is in general referred to as "GLP-1 (active)"; measurement intended for a total amount of GLP-1 generated from full length GLP-1 that is referred to as "GLP-1 (total)" including active form GLP-1, inactive form GLP-1, and full length GLP-1; or the like. A method of measuring the amount of each of GLP-1 in itself is not limited and can be carried out by a well known immunological analysis, instrumental analysis, or the like. Preferred is an immunological method and, for example, an enzyme immunoassay, competitive RIA method, or the like is preferably employed. As the enzyme immunoassay, a method utilizing, for example, absorption of light, fluorescence, chemiluminescence, or the like is employed. Among these, a fluorescence method or chemiluminescence method is in particular preferably used. The measurement can also be carried out by using a commercially available EIA, ELISA, or RIA kit.

In the present invention, the phrase "subjecting a sample in advance to an acid treatment" refers to treating a sample with an acidic solution before subjecting it to the above-mentioned step of measuring the amount of GLP-1. For instance, an acidic solution is added to a sample and the resultant is incubated at room temperature or 37° C. for a certain period of time. A certain period of time is preferably about 10 to 30 minutes. Further, the resultant may thereafter be neutralized with an alkaline solution, and this embodiment can be also referred to as the acid treatment. After adding the alkaline solution, it should be immediately mixed.

A sample to be used in the present invention is not restricted as long as it can be used in the above-mentioned measurement of the amount of GLP-1; and example thereof include the blood (including whole blood, blood plasma, and blood serum). The blood plasma can be preferably used.

An acid treatment in the present invention is a method of inhibiting influence to the above-mentioned measurement of the amount of GLP-1, wherein GLP-1 is denatured whereas foreign substances other than GLP-1 that cause non-specific reactions are denatured or the like.

Any acidic solution may be used in the acid treatment of the present invention as long as the acidic solution is capable of, without denaturing GLP-1, denaturing foreign substances other than GLP-1 which cause non-specific reactions, and does not affect a subsequent measurement. Such an acidic solution can be selected from known acidic solutions by those skilled in the art without excessive trial and error. The acidic solution is, for example, an acidic solution with a pH of 4 or less. It is more preferred to be an acidic solution with a pH of 2.5 or less. The lower limit of the pH of the acidic solution is not particularly restricted and is, for example, pH 1 or more. Concrete examples include a solution containing at least one of glycine (aminoacetic acid), hydrochloric acid, acetic acid, guanidine hydrochloride, sulfuric acid, and phosphoric acid. A suitable pH varies according to each of the acids and can be readily determined by those skilled in the art. Usually, the lower pH is more preferred. Further, an acidic solution having a buffering ability is preferred because it is able to make up with deviation in operability. Examples thereof include a glycine-hydrochloric acid buffer solution, hydrochloric acid-potassium chloride buffer solution, citric acid buffer solution, acetic acid buffer, and citric acid-phosphate buffer solution. The use of the acidic solution like this is able to denature only non-specific reactive substances and therefore allows for an accurate measurement exclusively of GLP-1. Further, because the denatured non-specific reactive substance is difficult to precipitate and/or deposit, the sample can be subjected to the measurement without going through removal operations by centrifugation and/or precipitation after the pretreatment, thereby leading to simple and convenient operation.

It is more preferred that the acidic solution be added at 1:9 to 1:1 in volume based on the sample solution.

After the acid treatment is carried out, for the purpose of eliminating influence on the above-mentioned measurement of the amount of GLP-1, an alkaline solution is preferably added for neutralization such that the pH becomes about 7. Any alkaline solution may be usable for the neutralization as long as the solution is one that does not affect the measurement; and the alkaline solution can be selected from known alkaline solutions by those skilled in the art without excessive trial and error. Examples thereof include tris, sodium hydroxide, potassium hydroxide, ammonia, sodium carbonate, and sodium bicarbonate. Further, an alkaline solution having a buffering ability is preferred because it is able to make up with deviation in operability. Examples thereof include a tris hydrochloric acid buffer solution, phosphate buffer solution, glycine-sodium hydroxide buffer solution, and carbonic acid-bicarbonate buffer solution.

A kit of the present invention can be used for carrying out of the measurement method of the present invention and is characterized by containing an acidic solution for subjecting a sample in advance to an acid treatment. To be specific, (a) the acidic solution,
(b) an antibody specific to GLP-1, and
(c) an instruction manual are contained.

As for the above-mentioned antibody to be used in the kit of the present invention, it can be either a monoclonal antibody or polyclonal antibody. In addition, the antibody can be used in the kit as an antibody fragment that retains an ability to specifically bind to GLP-1 such as Fab, Fab', F(ab')2, or Fv.

Further, the above-mentioned antibody can be used in the kit as it is or can be used in the kit in a form suitable for an utilized immunological technique, for example, in a state of being immobilized to a latex carrier when a latex agglutination immunoassay is employed, in a state of being immobilized to magnetic particles when a highly-sensitive measurement method using the magnetic particles or the like is employed, in a state of being immobilized to a base material when a method using the base material such as an immunochromatography method or the like is employed, or in a state of being labeled when labeling with a labeling substance (for example, an enzyme, fluorescent substance, chemoluminescence substance, radioactive isotope, biotin, avidin) is required.

Further, the above-mentioned instruction manual to be included in the kit of the present invention is not particularly restricted as long as it mentions the in-advance treatment of a sample with an acidic solution. The instruction manual can include, in addition to what is mentioned above, for example, explanation about implementation procedures of an immunological measurement using the kit of the present invention, precautions on storage and handling of the kit itself, and the like.

It is to be noted that even if the acidic solution for carrying out the acid treatment is separate from reagents for measuring GLP-1, as long as it is used for subjecting a sample in advance to the acid treatment when GLP-1 is measured, the acidic solution is substantially comprised in the kit of the present invention.

EXAMPLES

By way of examples the present invention will now be concretely described below. However, the present invention is by no means limited to the mode of the following examples.

Example 1

Procedures of the Measurement Method by the Acid Treatment of the Present Invention and a Conventional Measurement Method by a Solid Phase Column 1-1: Procedures of the Measurement Method by the Acid Treatment of the Present Invention
1-1-1: Samples As for samples, healthy individuals were used as subjects; diprotin A was added to an EDTA blood collection tube (manufactured by NIPRO Corporation) according to Japanese Patent Application Laid-Open Publication No. 2008-104870; the blood was collected at the time of fasting or after meal loading; and individual blood plasma was used in the measurement below.

1-1-2: Standard Sample Solution for Standard Curve

As a standard substance, Glucagon-like Peptide 1 (Human, 7-36 Amide) (manufactured by Peptide Institute, Inc.) was used. Solutions with eight levels of concentrations, 0 and 1 to 100 pmol/L, were prepared and used for quantification.

1-1-3: Acid Treatment

To a tube made of polypropylene, 150 μL of 0.2 mol/L glycine-hydrochloric acid buffer solution (pH 1.3) and a standard sample solution for a standard curve or 150 μL of individual blood plasma were added and mixed. The resulting mixture was incubated at 37° C. for 10 minutes. Thereafter, 30 μL of 2 mol/L tris hydrochloric acid buffer solution (pH 8.5) was added thereto for neutralization and used as a sample subjected the acid treatment in the following measurement of the amount of active form GLP-1.

1-1-4: Measurement of Concentration of Active Form GLP-1

For the measurement of the concentration of active form GLP-1, GLUCAGON-LIKE PEPTIDE-1 (ACTIVE) ELISA KIT 96 Well Plate (manufactured by Merck Millipore) by an anti-GLP-1 monoclonal antibody was used. The measurement method was carried out according to an accompanying explanatory leaflet. As for a measurement apparatus, Veritas microtiter plate luminometer (manufactured by Promega) was used; and the analysis was carried out by SoftMax Pro (manufactured by Molecular Devices Japan).

1-2: Procedures of a Conventional Measurement Method by a Solid Phase Column The procedure was carried out in the same manner as described in 1-1 except that the acid treatment of 1-1-3 was altered to the following solid phase column.

As the solid phase column, Oasis HLB Extraction Plate (manufactured by Waters Corporation) was used. It was used according to the accompanying instruction manual. After the conditioning of column was carried out, 300 µL of the blood plasma prepared in 1-1-1 was diluted 4-fold with PBS to 1200 µL, which was added to a well and then subjected to centrifugation (10×g, for 3 minutes, room temperature). Thereafter, 10% methanol solution 1 mL was added and then subjected to centrifugation (10×g, for 3 minutes, room temperature) to wash the well. This operation was repeated twice. Subsequently, a deep well plate was set up and 0.5 mL of 75% methanol solution containing 0.5% ammonia was added and then subjected to centrifugation (10×g, 3 minutes, room temperature) for elution. After repeating this operation twice, the eluting solution was completely collected from the well by centrifugation (100×g, for 1 minute, room temperature). Subsequently, this eluting solution was dried to solidify under a nitrogen stream. To this, 250 µL of Assay Buffer contained in GLUCAGON-LIKE PEPTIDE-1 (ACTIVE) ELISA KIT 96 Well Plate kit (manufactured by Merck Millipore) was added, put through a plate shaker for about 5 minutes for re-dissolution, and used in the measurement of the concentration of active form GLP-1 as a pretreated sample. Because a re-dissolved amount of 250 µl, was less than the amount of the sample, which was 300 µL, a measurement value was multiplied by a volume correction coefficient (0.83: a value obtained by dividing the re-dissolved amount by the amount of the sample).

Further, in cases where the pretreatment was not carried out by way of comparison, the blood plasma prepared in 1-1-1 was used as was in the measurement of the concentration of active form GLP-1 (the volume correction was not required either).

Example 2

Comparison of Effects of Pretreatment Methods in the Measurement of the Concentration of Active Form GLP-1

When the concentration of active form GLP-1 and the concentration of total GLP-1 are compared in the same individual, individuals whose concentration of active form GLP-1 is higher than their concentration of total GLP-1 were noted in a method without pretreatment. Thus, it was obvious that active form GLP-1 is not able to be accurately measured without the pretreatment and it has been confirmed that the pretreatment by a conventional solid phase column is effective.

Because the concentration of active form GLP-1 is a very low concentration (near the lower limit of quantification, 1 pmol/L) at the time of fasting, it becomes possible to accurately check the influence of non-specific reactive substances to measurement values by measuring the fasting blood plasma.

According to Example 1, the concentration of active form GLP-1 was measured by each of the pretreatment methods.

The blood plasma was individually prepared from 29 cases of healthy subjects at the time of fasting. The blood plasma was treated by a method without pretreatment, a solid phase column method, or an acid treatment method and then the concentration of active form GLP-1 was measured. Among these, because the measurement value in the solid phase column method was relatively low due to loss by the pretreatment, the result obtained by subjecting the measurement value to recovery rate correction (measurement value/0.75) was used for comparison for the sake of convenience. As a result, the result equivalent to the solid phase column method was obtained by the acid treatment method of the present invention. The results are shown in FIG. 1.

A non specific increase in the value was noted in many samples without the pretreatment, whereas such an increase could be significantly inhibited by the pretreatment of the sample by the acid treatment method. Further, for the sake of convenience, values were determined by subjecting the measurement value to recovery rate correction in a solid phase column method. But, the recovery rate was not always stable; and it was uncertain if the measurement value was correct. However, the value in the acid treatment method was, without the use of such a correction coefficient, equivalent to the measurement value after the correction in the solid phase column method. It was thus found that the measurement value was able to be obtained in a simple and highly accurate fashion. From the above, it was demonstrated that the measurement result was able to be stably and accurately obtained by the acid treatment.

Example 3

Comparison of Effects of the Pretreatment Methods in the Measurement of the Concentration of Active Form GLP-1

According to Example 1, the concentration of active form GLP-1 for 10 cases of healthy subjects after meal loading was measured by each of the pretreatment methods.

Because the concentration of endogenous active form GLP-1 increases by the meal loading, it becomes possible to confirm that, by measuring the blood plasma after the meal loading, the acid treatment method does not affect the measurement of the concentration of endogenous active form GLP-1.

Figure 2:
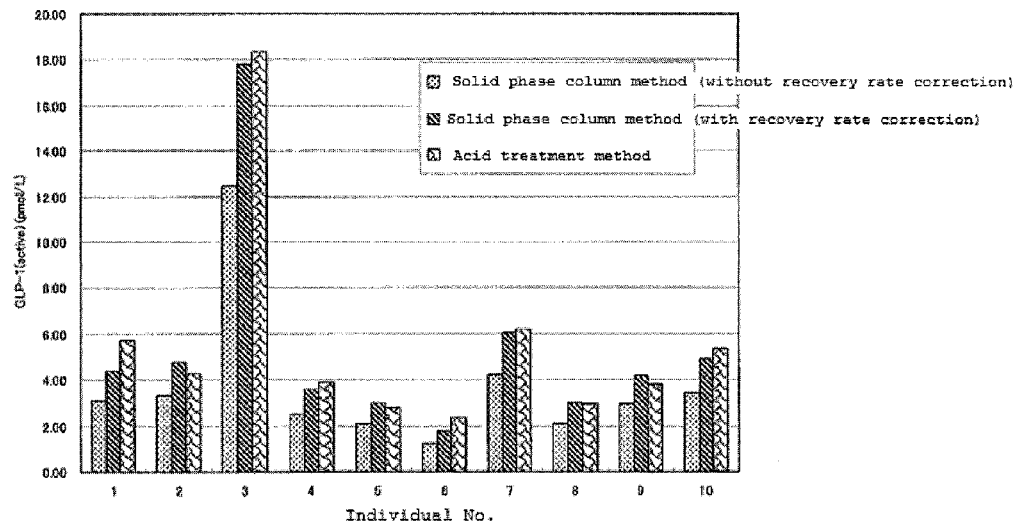
FIG. 2 shows the result obtained by treating the blood plasma after meal loading by a solid phase column method (with or without correction) or an acid treatment method and by subsequently measuring the concentration of active form GLP-1.

The blood plasma was individually prepared from 10 cases of healthy subjects after meal loading. The blood plasma was treated by a solid phase column method and an acid treatment method; and then the concentration of active form GLP-1 was measured. Among these, because the measurement value in the solid phase column method was relatively low due to loss by the pretreatment, the result obtained by subjecting the measurement value to recovery rate correction (measurement value/0.75) was also used for comparison for the sake of convenience. As a result, the result equivalent to the solid phase column method with recovery rate correction was obtained by the acid treatment method of the present invention; and it was found that the acid treatment method of the present invention was able to accurately measure the concentration of active form GLP-1. The results are shown in FIG. 2.

In the same manner as Example 2, it was found that, regardless of the level of skills of those who carry out measurement or difference among the lots of the column, the measurement value was able to be stably obtained in a simple and highly accurate fashion by the acid treatment method.

Example 4

Comparison of Acid Treatment Conditions in Various Types of Acids

According to Example 1 and the following Tables 1, two cases of individual blood plasma at the time of fasting or after meal loading were each measured and the chemiluminescence intensity was compared in a method without pretreatment, a solid phase column method, and an acid treatment method and; then the concentration of active form GLP-1 was measured. Because the chemiluminescence intensity in the solid phase column method was relatively low due to loss by the pretreatment, the result obtained by subjecting the chemiluminescence intensity to recovery rate correction (chemiluminescence intensity/0.75) was used for comparison for the sake of convenience. All of the acid treatment solutions were added in an amount equal to the individual blood plasma (150 µL). Table 1 shows the type of acid treatment solution and condition of neutralization other than the condition of the acid treatment shown in Example 1. With regard to the acid treatment method, the result obtained by carrying out volume correction {the chemiluminescence intensity×(the amount of individual blood plasma+the amount of the acid treatment solution+the amount of neutralization solution added)/(individual blood plasma amount+the amount of the acid treatment solution)} to the amount of added neutralization solution was used.

TABLE 1

| Acid treatment solution | Neutralization solution | Amount of added neutralization solution (µL) |
|---|---|---|
| 0.2 mol/L glycine-hydrochloric acid buffer solution (pH 2.5) | 1 mol/L tris hydrochloric acid buffer solution (pH 8.5) | 20 |
| 0.2 mol/L glycine-hydrochloric acid buffer solution (pH 3.0) | 0.5 mol/L tris hydrochloric acid buffer solution (pH 8.5) | 20 |
| 0.2 mol/L glycine-hydrochloric acid buffer solution (pH 3.5) | 0.25 mol/L tris hydrochloric acid buffer solution (pH 8.5) | 20 |
| 0.2 mol/L glycine-hydrochloric acid buffer solution (pH 4.0) | 0.05 mol/L tris hydrochloric acid buffer solution (pH 8.5) | 25 |
| HCl (pH 1.3) | 1 mol/L tris hydrochloric acid buffer solution (pH 8.5) | 30 |
| HCl (pH 2.5) | 0.1 mol/L tris hydrochloric acid buffer solution (pH 8.5) | 20 |
| HCl (pH 3.0) | 0.05 mol/L tris hydrochloric acid buffer solution (pH 8.5) | 30 |
| HCl (pH 3.5) | 0.05 mol/L tris hydrochloric acid buffer solution (pH 8.5) | 20 |
| HCl (pH 4.0) | 0.025 mol/L tris hydrochloric acid buffer solution (pH 8.5) | 20 |
| Acetic acid (pH 2.5) | 2 mol/L NaOH | 30 |
| Acetic acid (pH 3.0) | 0.5 mol/L tris hydrochloric acid buffer solution (pH 8.5) | 30 |
| Acetic acid (pH 3.5) | 0.1 mol/L tris hydrochloric acid buffer solution (pH 8.5) | 30 |
| Acetic acid (pH 4.0) | 0.1 mol/L tris hydrochloric acid buffer solution (pH 8.5) | 20 |

Figure 3:
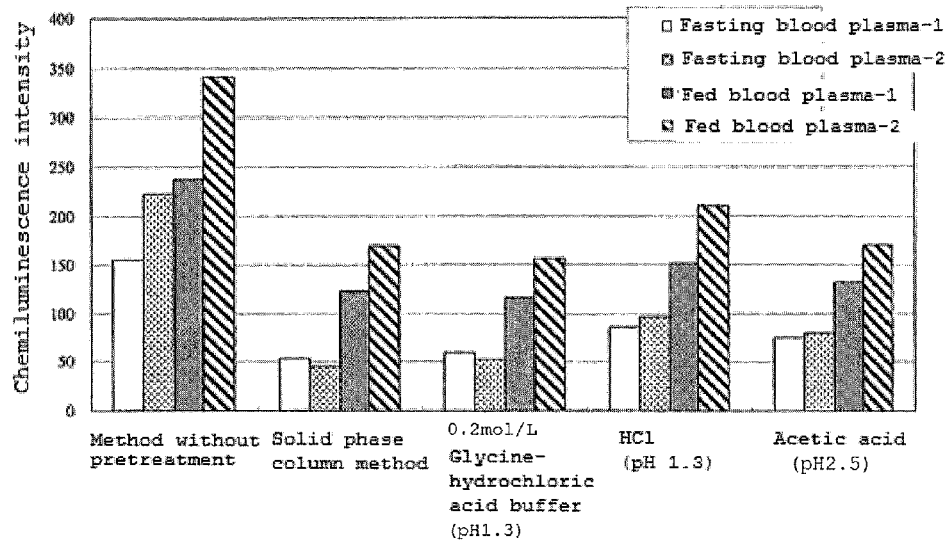
FIG. 3 shows the result obtained by measuring the concentration of active form GLP-1 in the fasting blood plasma and blood plasma after meal loading which were treated using various types of acids.

The results are shown in FIG. 3 and Table 2.

TABLE 2

Comparison of each chemiluminescence intensity difference to a solid phase column method

| | Fasting blood plasma-1 | Fasting blood plasma-2 | Blood plasma after meal loading-1 | Blood plasma after meal loading-2 |
|---|---|---|---|---|
| 0.2 mol/L glycine-hydrochloric acid buffer solution | | | | |
| Solid phase column method | 54 | 45 | 123 | 169 |
| pH 1.3 | +6.6 | +7.5 | −6.6 | −12.9 |
| pH 2.5 | +50.0 | +84.4 | +65.4 | +101.8 |
| pH 3.0 | +30.1 | +71.8 | +77.7 | +158.7 |
| pH 3.5 | +33.0 | +67.5 | +62.3 | +156.0 |
| pH 4.0 | +34.2 | +70.3 | +56.7 | +183.6 |
| Method without pretreatment | +101.7 | +177.1 | +114.8 | +172.2 |
| HCl | | | | |
| Solid phase column method | 54 | 45 | 123 | 169 |
| pH 1.3 | +32.5 | +51.0 | +28.8 | +40.5 |
| pH 2.5 | +24.9 | +58.7 | +60.3 | +166.4 |
| pH 3.0 | +28.4 | +55.0 | +77.8 | +161.3 |
| pH 3.5 | +34.1 | +57.4 | +90.6 | +168.0 |
| pH 4.0 | +20.7 | +49.9 | +52.3 | +113.2 |
| Method without pretreatment | +101.7 | +177.1 | +114.8 | +172.2 |
| Acetic acid | | | | |
| Solid phase column method | 54 | 45 | 123 | 169 |
| pH 2.5 | +21.7 | +34.8 | +10.1 | +0.8 |
| pH 3.0 | +31.4 | +52.5 | +70.6 | +137.6 |
| pH 3.5 | +24.9 | +50.5 | +63.4 | +139.4 |
| pH 4.0 | +19.0 | +57.8 | +70.2 | +163.7 |
| Method without pretreatment | +101.7 | +177.1 | +114.8 | +172.2 |

As a result, a variation of +101.7 to +177.1 was noted in the chemiluminescence intensity difference in the method without pretreatment, as compared with the solid phase column. It was confirmed that, in all of the acids, namely a glycine-hydrochloric acid buffer solution, HCl, and acetic acid, the variation in the chemiluminescence intensity difference to the solid phase column method became smaller, as compared with the method without pretreatment. In particular, it was noted that, in the glycine-hydrochloric acid buffer solution (pH 1.3), HCl (pH 1.3), and acetic acid (pH 2.5), the chemiluminescence intensity difference to the solid phase column method, which was −12.9 to +51.0, tended to become further smaller: and it became clear that a condition where the pH is low was desired. Among these, it was shown that, in cases where the acid treatment was carried out in the glycine-hydrochloric acid buffer solution (pH 1.3), the effect of removing non-specific reactive substances was highest (the chemiluminescence intensity difference to the solid phase column method: −12.9 to +7.5); and the result equivalent to the solid phase column method was able to be obtained.

Example 5

Comparison of Effects of the Pretreatment Methods in the Measurement of the Concentration of Active Form GLP-1

According to Example 1, the concentration of active form GLP-1 was measured by each of the pretreatment methods.

Figure 4:
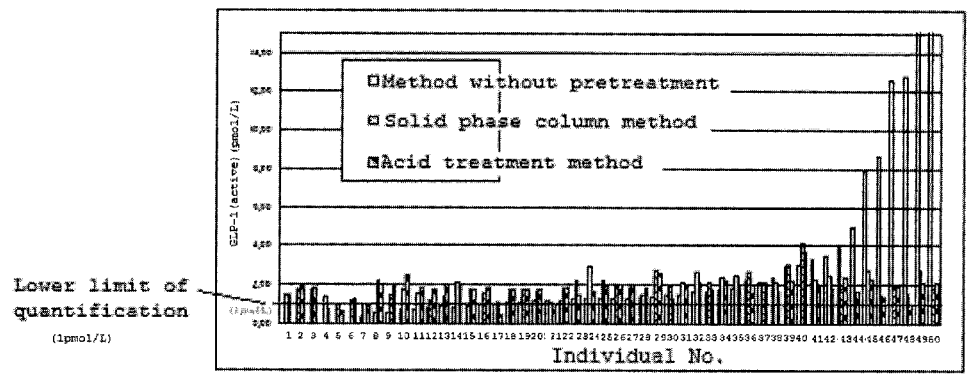
FIG. 4 shows the result obtained by treating the fasting blood plasma by a method without pretreatment, a solid phase column method, or an acid treatment method for 50 cases of other healthy subjects and by subsequently measuring the concentration of active form GLP-1.

The blood plasma was individually prepared from 50 cases of healthy subjects at the time of fasting. The blood plasma was treated by a method without pretreatment, a solid phase column method, or an acid treatment method and then the concentration of active form GLP-1 was measured. Among these, because the measurement value in the solid phase column method was relatively low due to loss by the pretreatment, the result obtained by subjecting the measurement value to recovery rate correction (measurement value/0.75) was used for comparison for the sake of convenience. As a result, the result equivalent to the solid phase column method was obtained by the acid treatment method of the present invention. The results are shown in FIG. 4.

Example 6

Comparison of Effects of the Pretreatment Methods in the Measurement of the Concentration of Active Form GLP-1

According to Example 1, by each of the pretreatment methods, the concentration of active form GLP-1 of 50 cases of healthy subjects after meal loading was measured.

Figure 5:
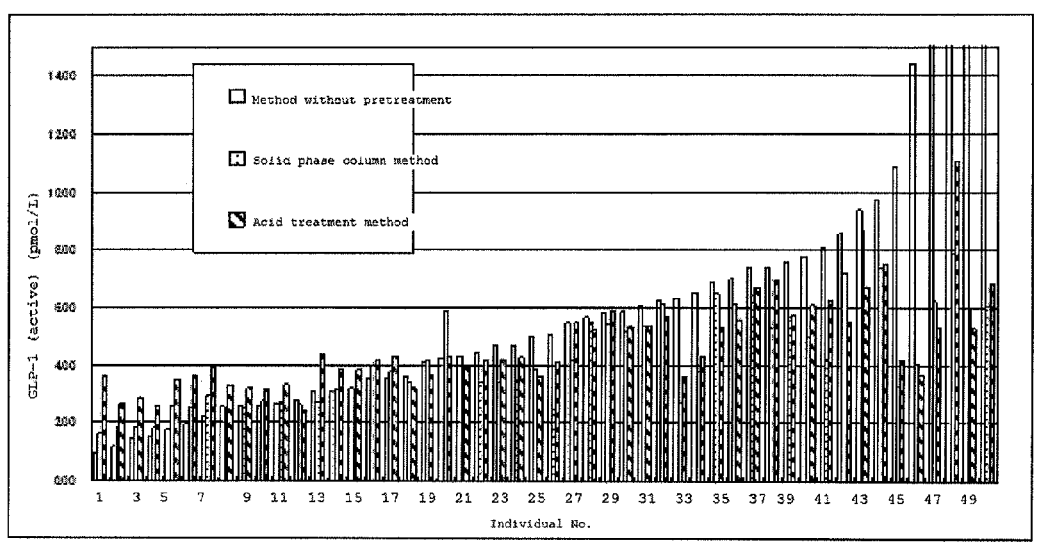
FIG. 5 shows the result obtained by treating the blood plasma after meal loading by a method without pretreatment, a solid phase column method, or an acid treatment method for 50 cases of other healthy subjects and by subsequently measuring the concentration of active form GLP-1.

The blood plasma was individually prepared from 50 cases of healthy subjects after meal loading. The blood plasma was treated by a solid phase column method and an acid treatment method and then the concentration of active form GLP-1 was measured. Among these, because the measurement value in the solid phase column method was relatively low due to loss by the pretreatment, the result obtained by subjecting the measurement value to recovery rate correction (measurement value/0.75) was also used for comparison for the sake of convenience. As a result, the result equivalent to the solid phase column method with recovery rate correction was obtained by the acid treatment method of the present invention; and it was found out that the acid treatment method of the present invention was able to accurately measure the concentration of active form GLP-1. The results are shown in FIG. 5.

Example 7

Comparison of the Correlativity of Measurement Values in Each of the Pretreatment Methods Of the measurement values of 100 cases obtained in Examples 5 and 6, the measurement values of 97 cases that were in a quantification range were subjected to an analysis using regression analysis.

Figure 6:
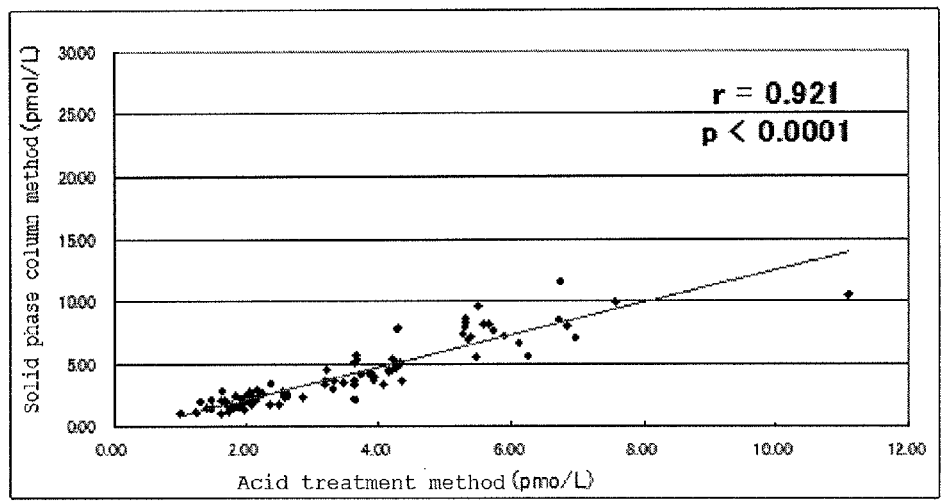
FIG. 6 shows the result obtained by analyzing, on the basis of the results Examples 5 and 6, the correlativity of each of the combinations among a method without pretreatment, a solid phase column method, and an acid treatment method.
Figure 6:
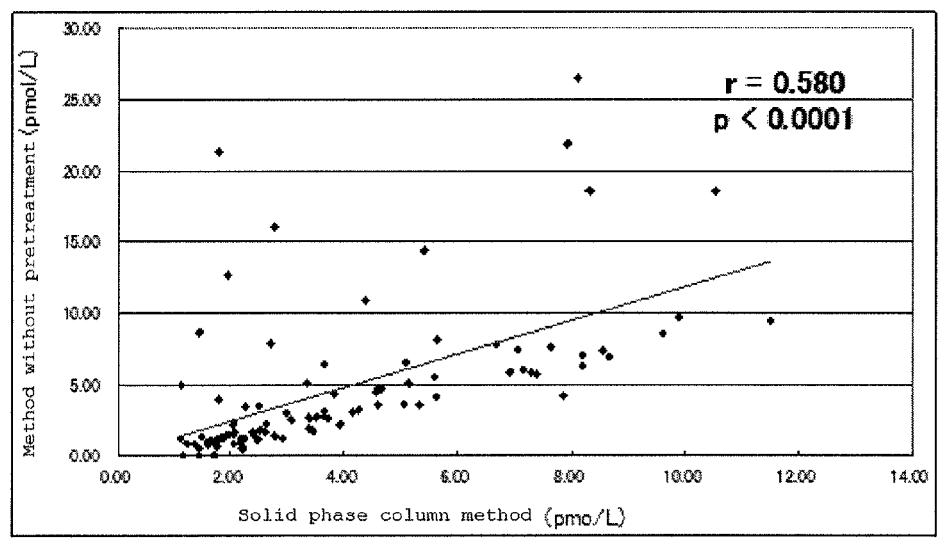
Figure 6:
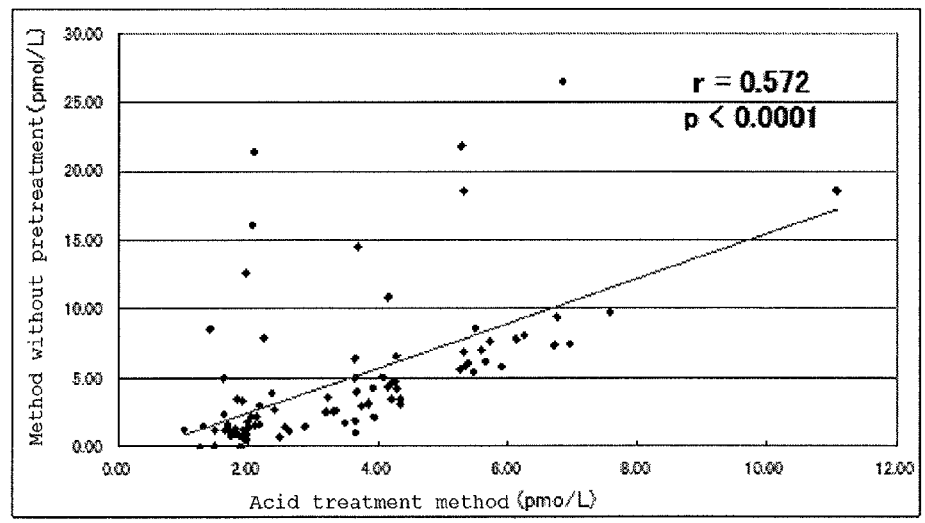

As a result, the correlation between the acid treatment method and solid phase column method was best (r=0.921). The results were shown in FIG. 6.

Industrial Applicability

The present invention can be used when the concentration of GLP-1 that is active in the blood (GLP-1 (active)) or the concentration of the total GLP-1 (GLP-1 (total)) is measured for the purpose of evaluating effects of drugs or food products aiming at treatment and/or prophylaxis of diabetes in the development thereof or the like. Because such a GLP-1 is able to be simply and accurately measured according to the present invention, the invention is of great use.

The invention claimed is:

1. A method of measuring the presence and/or an amount of glucagon-like peptide-1 (GLP-1) in a sample isolated from a subject, comprising treating said sample isolated from a subject with an acidic solution, neutralizing the acidic solution and then measuring the presence and/or an amount of GLP-1 in the sample, wherein the acidic solution has a pH of 2.5 or less.

2. The method according to claim 1, wherein said acidic solution comprises at least one of glycine, hydrochloric acid, sulfuric acid, and phosphoric acid.

3. The method according to claim 1, wherein said sample is blood.

4. The method according to claim 1, wherein said method of measuring GLP-1 comprises an enzyme immunoassay or a competitive radioimmunoassay.

5. A kit of measuring the presence and/or an amount of GLP-1 in a sample, comprising:

(a) an acidic solution having a pH of 2.5 or less,
(b) an antibody specific to GLP-1,
(c) an instruction manual, and
(d) an alkali solution for neutralization of the acidic solution.

6. The method according to claim 2, wherein said sample is blood.

7. The method according to claim 2, wherein said method of measuring GLP-1 comprises an enzyme immunoassay or a competitive radioimmunoassay.

8. The method according to claim 3, wherein said method of measuring GLP-1 comprises an enzyme immunoassay or a competitive radioimmunoassay.

9. The method according to claim 6, wherein said method of measuring GLP-1 comprises an enzyme immunoassay or a competitive radioimmunoassay.

* * * * *